United States Patent
Cho et al.

(10) Patent No.: US 10,094,799 B2
(45) Date of Patent: Oct. 9, 2018

(54) ELECTRON MEDIATOR AND ELECTROCHEMICAL BIOSENSOR EMPLOYING THE SAME

(71) Applicant: Samsung Electronics Co., Ltd., Suwon-si (KR)

(72) Inventors: Seong-je Cho, Suwon-si (KR); Kwang-bok Kim, Incheon (KR); Jae-hong Kim, Incheon (KR); Su-ho Lee, Suwon-si (KR); Sun-tae Jung, Yongin-si (KR); Jae-geol Cho, Yongin-si (KR); Chul-ho Cho, Seongnam-si (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 14/834,064

(22) Filed: Aug. 24, 2015

(65) Prior Publication Data
US 2016/0054254 A1    Feb. 25, 2016

(30) Foreign Application Priority Data
Aug. 22, 2014   (KR) .................. 10-2014-0109959

(51) Int. Cl.
*G01N 27/327*   (2006.01)
*C12Q 1/00*   (2006.01)
*H01B 1/02*   (2006.01)

(52) U.S. Cl.
CPC .......... *G01N 27/3271* (2013.01); *H01B 1/02* (2013.01)

(58) Field of Classification Search
CPC .... C12Q 1/004; C12Q 1/006; G01N 27/3272; G01N 27/3271; H01B 1/02
See application file for complete search history.

(56) References Cited

U.S. PATENT DOCUMENTS

| | | | |
|---|---|---|---|
| 4,898,816 A | 2/1990 | Turner et al. | |
| 7,288,174 B2 | 10/2007 | Cui et al. | |
| 8,057,659 B2 | 11/2011 | Harding et al. | |
| 8,357,770 B2 | 1/2013 | Yoshimoto et al. | |
| 2004/0238359 A1* | 12/2004 | Ikeda | C12Q 1/004 204/403.1 |
| 2013/0081958 A1 | 4/2013 | Jung et al. | |
| 2014/0044608 A1* | 2/2014 | List | A61B 5/1455 422/410 |
| 2014/0102896 A1* | 4/2014 | Cho | C07F 15/025 204/403.14 |
| 2015/0008142 A1* | 1/2015 | Jeon | C12Q 1/004 205/777.5 |

FOREIGN PATENT DOCUMENTS

KR   20130035844   4/2013

* cited by examiner

*Primary Examiner* — Gurpreet Kaur
(74) *Attorney, Agent, or Firm* — McAndrews, Held & Malloy, Ltd.

(57) ABSTRACT

Provided is an electron mediator system, which may include a first transition metal complex and a second transition metal complex, wherein a working potential of the electron mediator system may be substantially the same as a molar average of a working potential of the first transition metal complex and a working potential of the second transition metal complex.

16 Claims, 2 Drawing Sheets

ELECTRON MEDIATOR AND ELECTROCHEMICAL BIOSENSOR EMPLOYING THE SAME

RELATED APPLICATION(S)

This application claims the benefit of Korean Patent Application No. 10-2014-0109959, filed on Aug. 22, 2014, in the Korean Intellectual Property Office, the disclosure of which is incorporated herein in its entirety by reference.

BACKGROUND

The present disclosure relates to an electron mediator, and more particularly, to an electron mediator applicable to an electrochemical biosensor. In addition, the present disclosure relates to electrochemical biosensor employing an electron mediator.

Biosensors are analytical sensors measuring a concentration or presence of a biological analyte. Examples of the biological analyte include glucose, cholesterol, lactate, creatinine, protein, peroxide, alcohol, amino acid, glutamic-pyruvic transaminase (GPT), and glutamic-oxaloacetic transaminase (GOT). An electrochemical biosensor detects the flow of electrons generated by the electrochemical oxidation or reduction of an analyte.

A representative example of biosensors is a blood glucose sensor. An electrochemical blood glucose sensor may include, for example, a working electrode and a counter electrode formed on an electrical insulating substrate; and a detecting reagent layer contacting the working electrode and the counter electrode. The detecting reagent layer in the electrochemical blood glucose sensor may include, for example, a glucose oxidase or a glucose dehydrase; an electron accepting coenzyme; and an electron mediator. When blood containing glucose is in contact with the detecting reagent layer, the glucose is oxidized by the glucose oxidase, forming electrons. The formed electrons may be transferred to the working electrode through the electron accepting coenzyme and the electron mediator. An ampere meter externally connected to between the working electrode and the counter electrode may detect a flow of electrons to measure oxidizing current of glucose. From the oxidizing current of glucose, the glucose concentration in the blood may be analyzed.

Most of the oxidases, dehydrases, and electron accepting coenzymes generally do not have ability or are very weak ability to directly transmitted electrons to an electrode. Therefore, the detecting reagent layer in the electrochemical biosensor needs to include an electron mediator. Examples of the electron mediator may include potassium ferricyanide $(K_3Fe(CN)_6)$, ferrocene, ferrocene derivatives, quinone derivatives, phenazine-methosulfate, methoxyphenazine-methosulfate, phenazine methyl sulfate, and dichloroindophenol. In particular, in the case of disposable blood glucose sensor, potassium ferricyanide $(K_3Fe(CN)_6)$ is most widely used as an electron mediator. Potassium ferricyanide $(K_3Fe(CN)_6)$ may be easily deteriorated by light, temperature, and humidity. Thus, in the case of long term storage, it is known that the precision of the biosensor decreases (refer to A Disposable Electrochemical Glucose Sensor Using Catalytic Subunit of Novel Thermostable Glucose Dehydrogenase, The Open Biotechnology Journal, 2007, 1, 26-30).

The electron mediator may serve to rapidly carry out electron transportation from an enzyme-coenzyme complex to an electrode. The enzyme-coenzyme complex obtained electrons from the analyte may be oxidized, transferring electrons to the electron mediator. The electron mediator, which received electrons from the enzyme-coenzyme complex, may be reduced. The reduced electron mediator may be oxidized to transfer electrons to the working electrode. Oxidation of the electron mediator may be carried out by the voltage applied to the working electrode (the voltage is with respect to the counter electrode). The voltage that may most effectively oxidize the electron mediator may be referred to as a working potential. The working potential may change depending on the combination of the electron mediator, the enzyme-coenzyme complex, and the electrode material.

It is noted that, if the working potential is excessively high, the working electrode may directly oxidize other materials rather than the analyte. Accordingly, an oxidizing current may be detected, which is greater than the oxidizing current that represents the actual concentration of the analyte. Accordingly, the concentration of the analyte may be determined to be greater than the actual concentration. Therefore, the working potential of the electron mediator needs to be lower than an oxidation voltage of materials other than the analyte.

Thus, the working potential of the electron mediator is required not only to be compatible with a selected combination of the enzyme-coenzyme complex and the electrode material, but also lower than the oxidation voltage of materials other than the analyte. However, it is very difficult to obtain an electron mediator that satisfies these requirements. It is because that a known electron mediator has an oxidation potential that is uniquely fixed. In addition, it is because that it is difficult to synthesize a new electron mediator that may exhibit the desired working potential and excellent electron transfer efficiency.

In order to achieve excellent electron transfer efficiency, the use of a combination of two different electron transfer materials as an electron mediator has been proposed (refer to: U.S. Pat. Nos. 4,898,816 and 8,057,659). In this case, the first electron transfer material may serve as a mediator that receives electrons from the enzyme-coenzyme complex, and the second electron transfer material may serve as a shuttle that transports electrons to the electrode. However, even in this case, it was not easy to adjust the working potential of the electron mediator system including the first electron transfer material and the second electron transfer material.

SUMMARY

Provided is an electron mediator system that may reproducibly and easily adjust a working potential.

Provided is a composition for forming a detecting reagent layer including the electron mediator system.

Provided is a biosensor including a detecting reagent layer including the electron mediator system.

Additional aspects will be set forth in part in the description which follows and, in part, will be apparent from the description, or may be learned by practice of the presented exemplary embodiments.

According to an aspect of an exemplary embodiment, an electron mediator system includes a first transition metal complex and a second transition metal complex, wherein a working potential of the electron mediator system is substantially the same as a molar average of a working potential of the first transition metal complex and a working potential of the second transition metal complex.

According to an aspect of another exemplary embodiment, a composition for forming a detecting reagent layer according to an embodiment may include the electron mediator system according to an embodiment; an enzyme; and a carrier.

According to another aspect of another exemplary embodiment, a biosensor may include a working electrode formed on an insulating substrate; a counter electrode formed on the insulating substrate; and a detecting reagent layer contacting the working electrode and the counter electrode, wherein the detecting reagent layer may include the electron mediator system according to an aspect of an exemplary embodiment.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
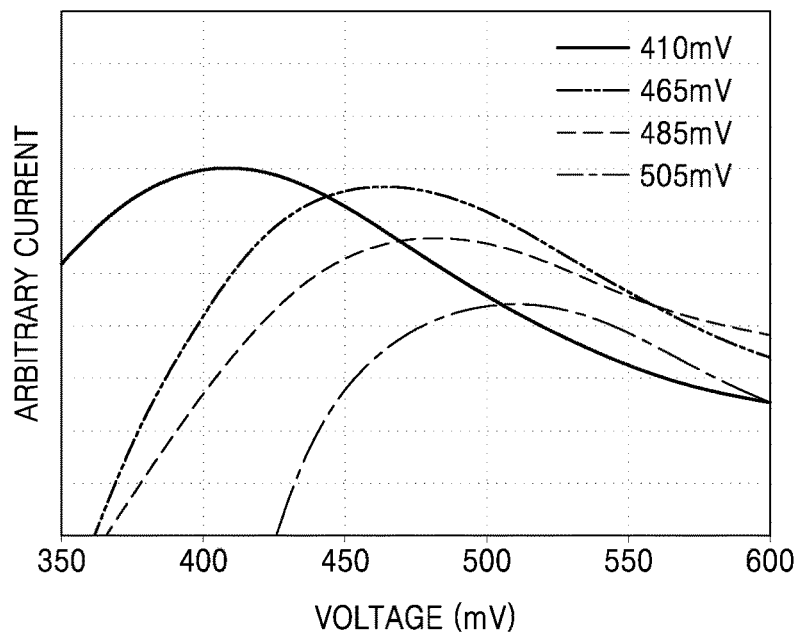
FIG. 1 is a graph illustrating current-voltage curves of an electron mediator system according to Example 1, depending on a change of a molar fraction of a first transition metal complex.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects.

Hereinafter an electron mediator system according to an aspect of an exemplary embodiment will be described in detail. According to an exemplary embodiment, an electron mediator system may include a first transition metal complex and a second transition metal complex, wherein a working potential of the electron mediator system may be substantially the same as a molar average of a working potential of the first transition metal complex and a working potential of the second transition metal complex.

A "molar average" of the working potential of the first transition metal complex and the working potential of the second transition metal complex may have a value of [(a working potential of the first transition metal complex×a molar fraction of the first transition metal complex)+(a working potential of the second transition metal complex×a molar fraction of the second transition metal complex)]. A molar fraction of the first transition metal complex has a value of (a mole number of the first transition metal complex)/(a mole number of the first transition metal complex+a mole number of the second transition metal complex). A molar fraction of the second transition metal complex has a value of (a mole number of the second transition metal complex)/(a mole number of the first transition metal complex+a mole number of the second transition metal complex).

The term "substantially the same" means that a working potential of the electron mediator system exhibits a linear relationship between a working potential of the first transition metal complex and a working potential of the second transition metal complex according to a molar fraction of the first transition metal complex, wherein a correlation factor ($R^2$) of the linear relationship may be, for example, about 0.95 or more, about 0.98 or more, or about 0.985 or more.

Accordingly, in the electron mediator system according to the present disclosure, by simply adjusting a molar fraction of the first transition metal complex (or, a molar fraction of the second transition metal complex), a desired working potential may be achieved. Accordingly, a new electron mediator may not be synthesized in order to realize a desired working potential that is compatible with a certain selected combination of an enzyme-coenzyme complex and an electrode material.

According to an embodiment, a primary ionization energy of the first transition metal complex and a primary ionization energy of the second transition metal complex may be similar to each other. If the primary ionization energy of the first transition metal complex is similar to the primary ionization energy of the second transition metal complex, electron transfer may be efficiently carried out between the first transition metal complex and the second transition metal complex. Accordingly, the first transition metal complex and the second transition metal complex may not exhibit their individual working potentials separately. Instead, the first transition metal complex and the second transition metal complex may exhibit a single combined working potential. Accordingly, if the primary ionization energy of the first transition metal complex is similar to the primary ionization energy of the second transition metal complex, the working potential of the electron mediator system may exhibit a linear relationship between the working potential of the first transition metal complex and the working potential of the second transition metal complex according to a molar fraction of the first transition metal complex. The fact that the primary ionization energy of the first transition metal complex is similar to the primary ionization energy of the second transition metal complex may mean, for example, that the difference between the primary ionization energy of the first transition metal complex and the primary ionization energy of the second transition metal complex may be about 15% or less, about 10% or less, about 5% or less, about 3% or less, about 1% or less, or about 0.5% or less. The percentage of the difference of ionization energy may be obtained by dividing an absolute value of the difference between a primary ionization energy of the first transition metal complex and a primary ionization energy of the second transition metal complex, by a higher value among the primary ionization energy of the first transition metal complex and the primary ionization energy of the second transition metal complex, followed by multiplying the resultant value by 100.

In some embodiments, the first transition metal complex may include a ligand that has an electrode bonding functional group (that is, a functional group capable of being bonded to an electrode). In this case, when a biosensor employing the electron mediator system according to an aspect of an exemplary embodiment is used, the first transition metal complex may uniformly attach to an electrode through the electrode bonding functional group. Accordingly, electrons transferred from the second transition metal complex to the first transition metal complex may be transferred to the electrode very effectively. Accordingly, if the primary ionization energy of the first transition metal complex is similar to the primary ionization energy of the second transition metal complex, and the first transition metal complex contains the electrode bonding functional group, the working potential of the electron mediator system may exhibit a more excellent linear relationship between the working potential of the first transition metal complex and the working potential of the second transition metal complex according to a molar fraction of the first transition metal complex.

For example, the electrode bonding functional group may be a thiophene group. The electrode bonding functional group may covalently bond to an electrode material, e.g., graphite.

For example, the ligand containing the electrode bonding functional group may be 5-(2,5-di-(thiopene-2-yl)-1H-pyrrol-1-yl)-1,10-phenanthroline.

For example, the first transition metal complex including the ligand containing the electrode bonding functional group may be 5-(2,5-di-(thiopene-2-yl)-1H-pyrrol-1-yl)-1,10-phenanthroline iron.

In some embodiments, the second transition metal complex may not contain the electrode bonding functional group. For example, the second transition metal complex not containing the electrode bonding functional group may be ferricyanide, hexaamineruthenium (II), or a combination thereof.

In some embodiments, the center metal of the first transition metal complex may be the same with the center metal of the second transition metal complex. In this case, the working potential of the electron mediator system may exhibit excellent linear relationship between the working potential of the first transition metal complex and the working potential of the second transition metal complex according to the molar fraction of the first transition metal complex. For example, the center metal of the first transition metal complex and the center metal of the second transition metal complex may be iron. For example, the first transition metal complex containing iron as a center metal may be 5-(2,5-di-(thiopen-2-yl)-1H-pyrrol-1-yl)-1,10-phenanthroline iron, and the second transition metal complex containing iron as a center metal may be ferricyanide.

In some embodiments, the center metal of the first transition metal complex may be different from the center metal of the second transition metal complex. For example, the center metal of the first transition metal complex may be iron, and the center metal of the second transition metal complex may be ruthenium. For example, the first transition metal complex containing iron as a center metal may be 5-(2,5-di-(thiopen-2-yl)-1H-pyrrol-1-yl)-1,10-phenanthroline iron, and the second transition metal complex containing ruthenium as a center metal may be hexaamineruthenium(II).

The working potential of the electron mediator system according to an aspect of an exemplary embodiment may be determined as follows: when measuring the current flowing from the working electrode to the counter electrode of a given biosensor, while varying the voltage applied to between the working electrode and the counter electrode, the voltage that generates the greatest current is determined as the working potential of the biosensor. Also, the working potential of the given biosensor may be determined as the working potential of the electron mediator system used in the given biosensor.

Hereinafter a composition for forming a detecting reagent layer according to another aspect will be described in detail. The composition for forming a detecting reagent layer according to an embodiment may include the electron mediator system according to an aspect of an exemplary embodiment; an enzyme; and a carrier.

As an enzyme, any suitable enzyme may be used that may selectively react with a biological analyte. In the electron mediator system according to an aspect of an exemplary embodiment, by simply adjusting the molar fraction of the first transition metal complex to the second transition metal complex, a desired working potential may be easily achieved. Therefore, very wide range of enzymes may be compatible with the electron mediator system according to an aspect of an exemplary embodiment.

Non-limiting examples of the enzyme may include a glucose oxidase, a glucose dehydrase, a cholesterol oxidase, a cholesterol esterase, a lactate oxidase, an ascorbic acid oxidase, an alcohol oxidase, an alcohol dehydrase, a bilirubin oxidase, a sugar dehydrase, or a combination thereof.

The composition for forming a detecting reagent layer may further include a coenzyme. Examples of the coenzyme may include a flavin adenine dinucleotide (FAD), a nicotinamide adenine dinucleotide (NAD), or a combination thereof.

The carrier may serve as a solvent or a dispersion medium for the electron mediator system and the enzyme. The carrier may be, for example, water, a buffer solution, or a combination thereof.

The composition for forming a detecting reagent layer may further include at least one additive selected from a surfactant, a water-soluble polymer, a quaternary ammonium salt, a fatty acid, and a thickening agent.

The surfactant may serve to allow the composition to be coated on an electrode in a uniform thickness while casting the composition. The surfactant may be, for example, Triton X-100, sodiumdodecyl sulfate, perfluorooctane sulfonate, or sodium stearate.

The water-soluble polymer may serve as a polymeric matrix of the detecting reagent layer. The water-soluble polymer may contribute in stabilizing and dispersion of an enzyme. The water-soluble polymer may be, for example, polyvinyl pyrrolidone (PVP), polyvinyl alcohol (PVA), poly fluoro sulfonate, hydroxyethyl cellulose (HEC), hydroxypropyl cellulose (HPC), carboxy methyl cellulose (CMC), cellulose acetate, or polyamide.

The quaternary ammonium salt may serve to reduce the measurement errors due to the amount of hematocrit. The quaternary ammonium salt may be, for example, ecyltrimethylammonium, myristyltrimethylammonium, cetyltrimethylammonium, octadecyltrimethylammonium, or tetrahexylammonium.

The fatty acid may serve to reduce the measurement errors due to the amount of hematocrit. In addition, the fatty acid may serve to extend a linear dynamic range of the biosensor in a high concentration range. The fatty acid may be, for example, a fatty acid or a salt thereof, having a $C_4$ to $C_{20}$ carbon chain. For example, the fatty acid may be, a fatty acid or a salt thereof, having a $C_6$ to $C_{12}$ alkyl carbon chain. Detailed example of the fatty acid may include a caproic acid, a heptanoic acid, a caprylic acid, an octanoic acid, a nonanoic acid, a capric acid, an undecanoic acid, a lauric acid, a tridecanoic acid, a myristic acid, a pentadecanoic acid, a palmitic acid, a heptadecanoic acid, a stearic acid, a nonadecanoic acid, or an arachidonic acid.

The thickening agent may serve to securely attach the detecting reagent layer to the electrode. The thickening agent may be, for example, hydroxyethylcellulose (e.g., Natrasol™) or diethyl amino ethyl-Dextran hydrochloride.

The composition for forming a detecting reagent layer may be coated on an electrode and then dried, to form a detecting reagent layer.

In addition, in the inventive concept, a biosensor according to another embodiment including a detecting reagent layer formed using the composition for forming a detecting reagent layer is provided. According to another aspect of the present disclosure, a biosensor may include a working electrode formed on an insulating substrate; a counter electrode formed on the insulating substrate; and a detecting reagent layer contacting the working electrode and the counter electrode, wherein the detecting reagent layer may include the electron mediator system according to an aspect of an exemplary embodiment.

The working electrode and the counter electrode may be formed on the same insulating substrate. Alternatively, the working electrode and the counter electrode may each separately be formed on different insulating substrates.

The biosensor may be used in analysis of glucose, cholesterol, lactate, creatinine, protein, peroxide, alcohol, amino acid, glutamic-pyruvic transaminase (GPT), or glutamic-oxaloacetic transaminase (GOT).

EXAMPLES

Example 1

In an electron mediator system, in which 5-(2,5-di-(thiopene-2-yl)-1H-pyrrol-1-yl)-1,10-phenanthroline iron was used as a first transition metal complex, and ferricyanide was used as a second transition metal complex, the working potential was measured with varying the molar fraction of the first transition metal complex.

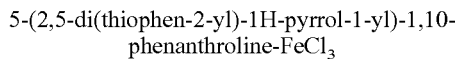

5-(2,5-di(thiophen-2-yl)-1H-pyrrol-1-yl)-1,10-phenanthroline-$FeCl_3$

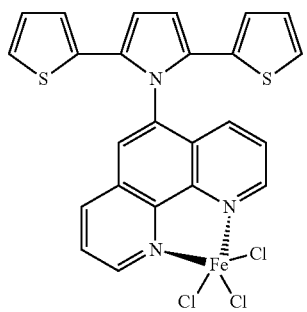

While changing the voltage applied to between the working electrode and the counter electrode of the biosensor, the current flowing from the working electrode to the counter electrode was measured. The voltage that generated the greatest current was determined as the working potential of the biosensor. In addition, the working potential of the biosensor was determined as the working potential of the electron mediator system. The measurement condition of the working potential was at a temperature of 25° C. and 1 atm (absolute atmosphere).

Figure 2:
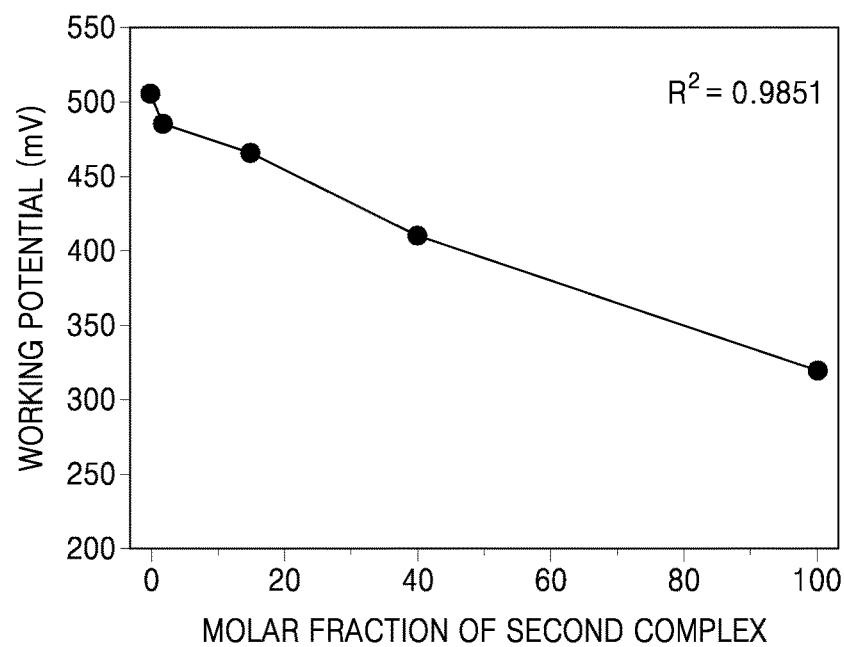
FIG. 2 is a graph illustrating a working potential of the electron mediator system according to Example 1, depending on a change of the molar fraction of the first transition metal complex.

FIG. 1 is a graph illustrating current-voltage curves of the electron mediator system according to Example 1, depending on the change of the molar fraction of the first transition metal complex (FIG. 1 also indicates the working potential for each curve; the molar fraction of the second transition metal complex for each curve is indicated in FIG. 2). It is noted that, in FIG. 1, each curve has a uni-modal shape having one maximum point. When two different types of electron transferring materials, each having a different oxidation potential, are used as an electron mediator, one of ordinary skill in the art commonly expect that a bi-modal current-voltage curve having two maximum points is obtained. However, as illustrated in FIG. 1, in the electron mediator system according to the present disclosure, uni-modal current-voltage curves were shown.

The working potential of the electron mediator system of Example 1 was determined from FIG. 1. FIG. 2 is a graph illustrating the working potential of the electron mediator system according to Example 1, depending on the change of the molar fraction of the first transition metal complex. As shown in FIG. 2, in the electron mediator system of Example 1, the molar fraction of the first transition metal complex and the working potential of the electron mediator system show a linear proportional relationship, wherein the correlation factor ($R^2$) is 0.9851, which is a quite high value.

Example 2

In an electron mediator system, in which 5-(2,5-di-(thiopene-2-yl)-1H-pyrrol-1-yl)-1,10-phenanthroline iron was used as a first transition metal complex, and hexaamineruthenium (II) chloride was used as a second transition metal complex, the working potential was measured with varying the molar fraction of the first transition metal complex.

While changing the voltage applied to between the working electrode and the counter electrode of the biosensor, the current flowing from the working electrode to the counter electrode was measured. The voltage that generated the greatest current was determined as the working potential of the biosensor. In addition, the working potential of the biosensor was determined as the working potential of the electron mediator system. The measurement condition of the working potential was at a temperature of 25° C. and 1 atm (absolute atmosphere).

Figure 3:
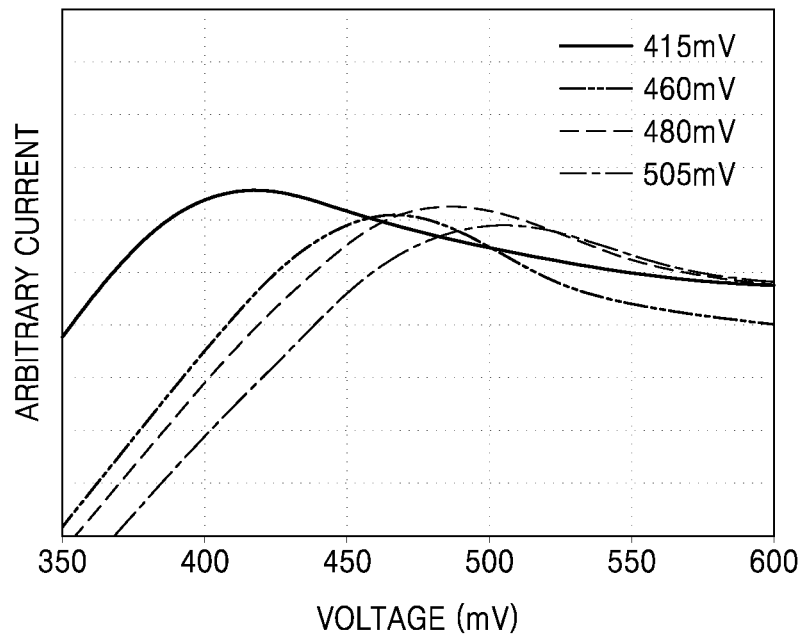
FIG. 3 is a graph illustrating current-voltage curves of an electron mediator system according to Example 2, depending on a change of a molar fraction of a first transition metal complex.
Figure 4:
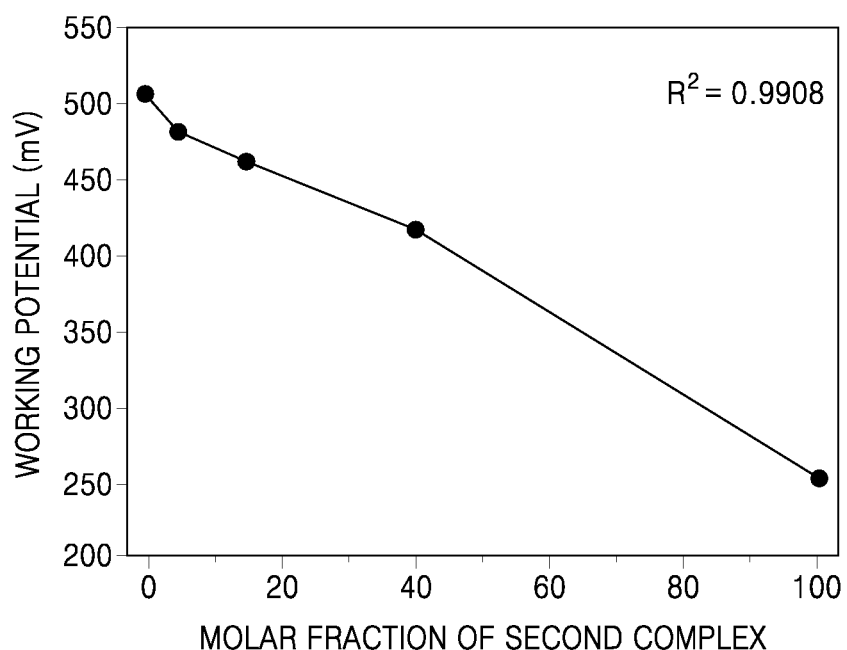
FIG. 4 is a graph illustrating a working potential of the electron mediator system according to Example 2, depending on the change of the molar fraction of the first transition metal complex.

FIG. 3 is a graph illustrating current-voltage curves of the electron mediator system according to Example 2, depending on the change of the molar fraction of the first transition metal complex (FIG. 3 also indicates the working potential for each curve; the molar fraction of the second transition metal complex for each curve is indicated in FIG. 4). It is noted that, in FIG. 3, each curve has a uni-modal shape having one maximum point. When two different types of electron transferring materials, each having a different oxidation potential, are used as an electron mediator, one of ordinary skill in the art commonly expect that a bi-modal current-voltage curve having two maximum points is obtained. However, as illustrated in FIG. 3, in the electron mediator system according to the present disclosure, uni-modal current-voltage curves were shown.

The working potential of the electron mediator system of Example 2 was determined from FIG. 3. FIG. 4 is a graph illustrating the working potential of the electron mediator system according to Example 2, depending on the change of the molar fraction of the first transition metal complex. As shown in FIG. 4, in the electron mediator system of Example 2, the molar fraction of the first transition metal complex and the working potential of the electron mediator system show a linear proportional relationship, wherein the correlation factor ($R^2$) is 0.9908, which is a quite high value.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An electron mediator system comprising a first transition metal complex and a second transition metal complex, wherein a working potential of the electron mediator system is substantially the same as a molar average of a working potential of the first transition metal complex and a working potential of the second transition metal complex, wherein the first transition metal complex comprises a ligand comprising a thiophene group.

2. The electron mediator system of claim 1, wherein the working potential of the electron mediator system exhibits a linear relationship between the working potential of the first transition metal complex and the working potential of the second transition metal complex according to a molar fraction of the first transition metal complex, wherein a correlation factor ($R^2$) of the linear relationship is 0.95 or greater.

3. The electron mediator system of claim 1, wherein a difference between a primary ionization energy of the first transition metal complex and a primary ionization energy of the second transition metal complex is 15% or less.

4. The electron mediator system of claim 1, wherein the first transition metal complex is 5-(2,5-di-(thiopene-2-yl)-1H-pyrrol-1-yl)-1,10-phenanthroline iron.

5. The electron mediator system of claim 1, wherein the second transition metal complex does not comprise an electrode bonding functional group.

6. The electron mediator system of claim 5, wherein the second transition metal complex is at least one of ferricyanide and hexaamineruthenium (II).

7. The electron mediator system of claim 1, wherein a center metal of the first transition metal complex is the same with a center metal of the second transition metal complex.

8. The electron mediator system of claim 1, wherein the first transition metal complex is 5-(2,5-di-(thiopen-2-yl)-1H-pyrrol-1-yl)-1,10-phenanthroline iron, and the second transition metal complex is ferricyanide.

9. The electron mediator system of claim 1, wherein a center metal of the first transition metal complex is different from a center metal of the second transition metal complex.

10. The electron mediator system of claim 1, wherein the first transition metal complex is 5-(2,5-di-(thiopen-2-yl)-1H-pyrrol-1-yl)-1,10-phenanthroline iron, and the second transition metal complex is hexaamineruthenium (II).

11. A composition for forming a detecting reagent layer comprising:
    an electron mediator system comprising a first transition metal complex and a second transition metal complex, wherein a working potential of the electron mediator system is substantially the same as a molar average of a working potential of the first transition metal complex and a working potential of the second transition metal complex;
    an enzyme; and
    a carrier,
    wherein the first transition metal complex comprises a ligand comprising a thiophene group.

12. The composition of claim 11, further comprising a coenzyme.

13. The composition of claim 11, wherein the working potential of the electron mediator system exhibits a linear relationship between the working potential of the first transition metal complex and the working potential of the second transition metal complex according to a molar fraction of the first transition metal complex, wherein a correlation factor ($R^2$) of the linear relationship is 0.95 or greater.

14. The composition of claim 11, wherein a difference between a primary ionization energy of the first transition metal complex and a primary ionization energy of the second transition metal complex is 15% or less.

15. The composition of claim 11, wherein the first transition metal complex is 5-(2,5-di-(thiopene-2-yl)-1H-pyrrol-1-yl)-1,10-phenanthroline iron.

16. A biosensor comprising:
    a working electrode formed on an insulating substrate;
    a counter electrode formed on the insulating substrate; and
    a detecting reagent layer contacting the working electrode and the counter electrode,
    wherein the detecting reagent layer comprises an electron mediator system that comprises a first transition metal complex and a second transition metal complex, wherein a working potential of the electron mediator system is substantially the same as a molar average of a working potential of the first transition metal complex and a working potential of the second transition metal complex,
    wherein the first transition metal complex comprises a ligand comprising a thiophene group.

* * * * *